(12) United States Patent
Gaon

(10) Patent No.: US 7,365,854 B2
(45) Date of Patent: Apr. 29, 2008

(54) APPARATUS AND METHODS FOR HIGH SPEED RGB COLOR DISCRIMINATION

(75) Inventor: Martin Gaon, Merrick, NY (US)

(73) Assignee: Nordson Corporation, Westlake, OH (US)

( * ) Notice: Subject to any disclaimer, the term of this patent is extended or adjusted under 35 U.S.C. 154(b) by 246 days.

(21) Appl. No.: 10/908,221

(22) Filed: May 3, 2005

(65) Prior Publication Data

US 2005/0254067 A1 Nov. 17, 2005

Related U.S. Application Data

(60) Provisional application No. 60/569,812, filed on May 11, 2004.

(51) Int. Cl.
*G01N 21/55* (2006.01)

(52) U.S. Cl. ...................... 356/448; 356/407

(58) Field of Classification Search ........ 356/445–448, 356/406, 425, 420, 402, 614, 407; 250/226
See application file for complete search history.

(56) References Cited

U.S. PATENT DOCUMENTS 3,910,701 A * 10/1975 Henderson et al. ........... 356/39
4,180,330 A * 12/1979 Kotera et al. ............... 356/425
4,603,976 A * 8/1986 Fetzer et al. ................ 356/402
4,668,979 A * 5/1987 Jung ........................... 358/515
4,678,338 A * 7/1987 Kitta et al. .................. 356/402
4,838,697 A 6/1989 Kurandt ...................... 356/406
4,917,500 A * 4/1990 Lugos ......................... 356/406
5,303,037 A * 4/1994 Taranowski ................. 356/406
2004/0179201 A1* 9/2004 Schnieder et al. ........... 356/445

* cited by examiner

*Primary Examiner*—Hoa Q. Pham
(74) *Attorney, Agent, or Firm*—Wood, Herron & Evans, LLP

(57) ABSTRACT

Device and method for inspecting a polychromatic region, such as a polychromatic pattern, on a moving workpiece. The method includes device includes a solid-state light source, preferably a light emitting diode, adapted to emit light in a range of wavelengths for illuminating the polychromatic region. Photodetectors are positioned relative to the workpiece to intercept light from the light source reflected by the polychromatic region. Each of the photodetectors is adapted to detect reflected light within a corresponding one of a plurality of bands defined within the range of wavelengths. The method includes detecting intensities of the light reflected from the polychromatic region within different wavelength bands in the range of wavelengths and evaluating a ratio of the intensities for comparison with a standard ratio to ascertain a variation in the evaluated ratio.

19 Claims, 2 Drawing Sheets

APPARATUS AND METHODS FOR HIGH SPEED RGB COLOR DISCRIMINATION

CROSS-REFERENCE TO RELATED APPLICATIONS

This application claims the benefit of U.S. Provisional Application No. 60/569,812, filed May 11, 2004, the disclosure of which is hereby incorporated by reference herein in its entirety.

FIELD OF THE INVENTION

This invention relates generally to material handling and, more particularly, to apparatus and methods for accurately assessing color information contained in light reflected from a moving workpiece by color discrimination.

BACKGROUND OF THE INVENTION

Color detection systems are used to sense polychromatic patterns impressed on a workpiece that carry data in coded form. For example, the polychromatic pattern may be a color bar code having individual bars that vary in color. Color detection systems quantify the colors contained in such polychromatic patterns by illuminating the pattern with a broad band spectrum or "white" light and measuring the spectral properties of the reflected light over the entire visible spectrum in comparison with the incident white light spectrum.

Generally, such color detection systems include a halogen lamp that functions as a constant light source of white light that illuminates the polychromatic pattern and one or more individual photodetectors that detect light reflected from the polychromatic pattern and workpiece. Color determination is being made by measuring and quantifying the intensity of the reflected light for different colors. The photodetectors are filtered spectrally using narrow band filters that transmit different wavelength ranges to define colorimetric values with respect to the individual color intensities in the light reflected from the polychromatic pattern. The colorimetric values are supplied to a computer for evaluation of the colors in the polychromatic pattern.

Color detection systems may be used in inspection systems that verify the characteristics of polychromatic printing on a package or carton blank. However, conventional techniques for evaluating the color intensities from such color detection systems are inappropriate due to the high line velocities found in many process lines. These high line velocities make absolute determinations of the shade or hue of a specific product color present in the polychromatic printing problematic because of the sheer number of successive workpieces that must be verified.

Generally, the color of the polychromatic printing determines the manner in which light is reflected from the polychromatic printing. When light is incident upon the workpiece, the reflected light will vary in intensity and wavelength dependent upon the individual colors in the polychromatic printing. The optical properties of the polychromatic printing are also affected by the manner in which light is reflected from the surface of the workpiece bearing the polychromatic printing. Specifically, specular or glossy surface finishes reflect light differently than diffuse objects or those that reflect light in all directions. Conventional color detection systems are especially limited in their ability to evaluate color intensities in light reflected from polychromatic printing on workpieces having specular surface finishes.

It would therefore be desirable to provide an improved inspection device and method for accurately assessing color information contained in polychromatic printing on each of a series of workpieces moving past the inspection device at a relatively high line speed.

SUMMARY OF THE INVENTION

In one embodiment of the present invention, a device includes a solid-state light source, preferably a light emitting diode, adapted to emit light in a range of wavelengths and a plurality of photodetectors. The light source is positioned for illuminating a polychromatic region, such as a polychromatic pattern, on a moving workpiece. The photodetectors are each positioned relative to the workpiece to intercept light from the light source reflected by the polychromatic region. Each of the photodetectors is adapted to detect reflected light within a corresponding one of a plurality of wavelength bands defined within the range of wavelengths.

In accordance with another aspect of the present invention, an inspection method comprises illuminating a moving workpiece with light that includes a range of wavelengths and reflecting a portion of the light from a polychromatic region on the workpiece. The method further includes detecting a first intensity of reflected light in a first wavelength range, detecting a second intensity of reflected light in a second wavelength range, and determining a ratio of the first intensity to the second intensity. The determined ratio is compared with a reference, such as a standard ratio, to detect a variation in the determined ratio relative to the reference.

In accordance with yet another aspect of the present invention, an inspection method includes illuminating each of a plurality of moving workpieces with light that includes a range of wavelengths. A ratio is determined of the light intensity reflected from a polychromatic region on each workpiece within a first wavelength band in the range of wavelengths to the light intensity reflected from the polychromatic region within a second wavelength band in the range of wavelengths. The method further includes comparing the determined ratio for first and second workpieces among the plurality of workpieces to detect a variation in a color in the polychromatic region between the first and second workpieces.

Various benefits and advantages of the invention shall be made apparent from the accompanying drawings of the illustrative embodiment and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENTS

Figure 1:
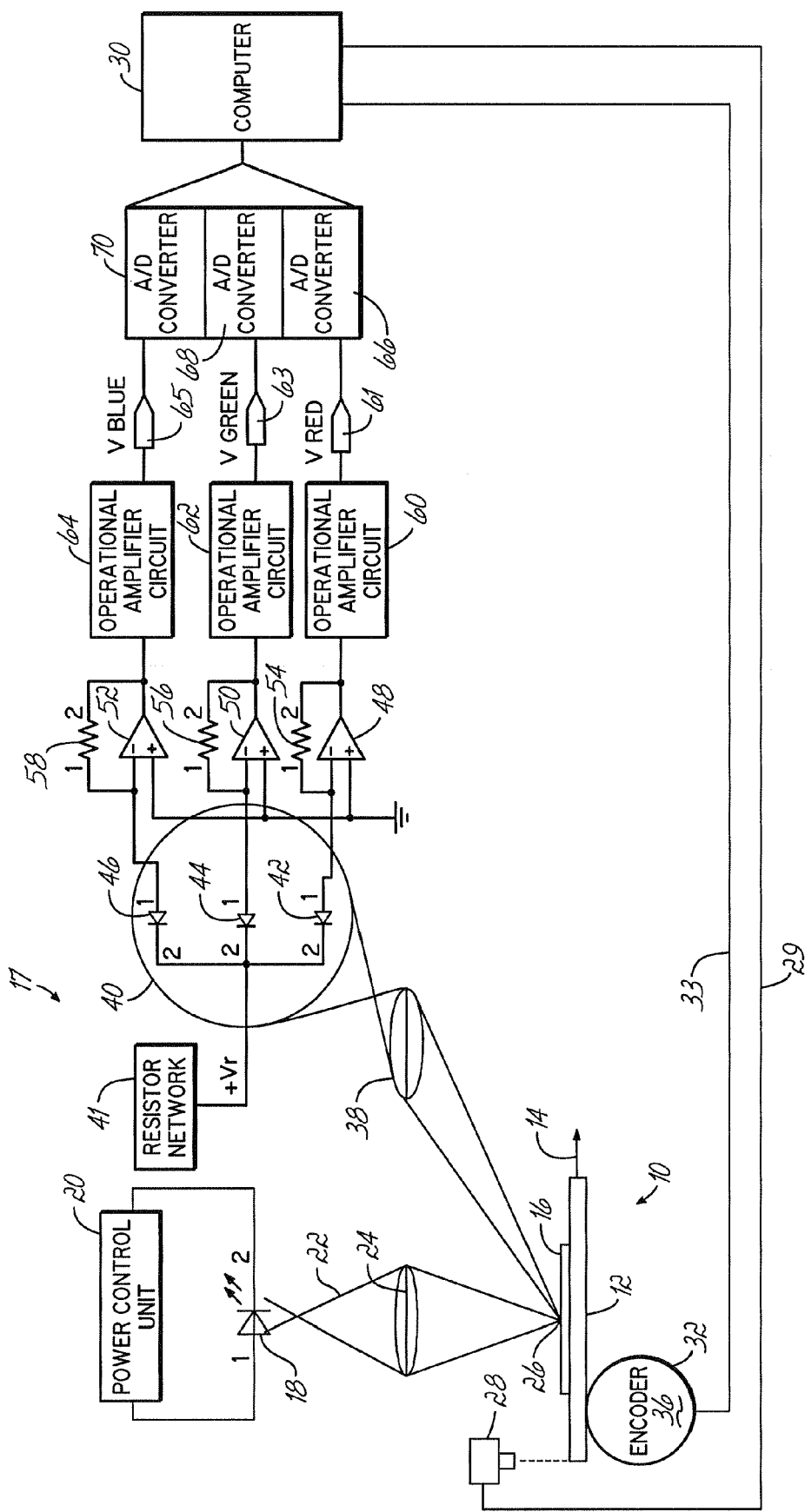
FIG. 1 is a diagrammatic view of an inspection system in accordance with an embodiment of the invention.

With reference to FIG. 1, a process line, generally indicated by reference numeral 10, includes a conveyor 12 moving in an upstream-to-downstream direction, generally indicated by a single-headed arrow 14. Conveyor 12 sequentially conveys or transfers a series of workpieces 16, such as cartons or box blanks, in a downstream direction as part of, for example, a packaging operation or a package assembly operation. The process line 10 may include, for example, a folder, an adhesive applicator, a printing press, a die cutter, or other conventional devices that process the stream of consecutive workpieces 16.

An inspection system, generally indicated by reference numeral 17, is positioned in proximity to a portion of the conveyor 12. The inspection system 17 is adapted to sense a polychromatic region, which is described hereinafter as being in the form of a polychromatic region 19 (FIGS. 2A, 2B), on each of the workpieces 16 transported by the conveyor 12 past inspection system 17. The polychromatic region 19 may be a single colored area on the surface of each workpiece 16 and may optionally cover the entire surface or a major portion of the surface of the workpiece 16 that is within the field of view of the inspection system 17. Alternatively, the polychromatic region 19 may include a pattern of different colors, or the polychromatic region 19 may include a pattern that represents coded indicia, such as a color bar code, capable of translation but ultimately not translated by the inspection system 17.

The inspection system 17 includes a light source 18, which has a light output controlled by an adjustable power control unit 20 and is stationary, positioned generally above the conveyor 12. The light source 18 emits a beam of light, diagrammatically indicated by reference numeral 22, at a constant distribution of wavelengths that preferably combine to produce white light. The incident light from light source 18 is focused by an illumination optical lens 24 to define a focused light spot 26 at a vertical location in the plane of the workpieces 16 arriving on the conveyor 12. Although the invention is not so limited, the beam of light from the light source 18 is typically incident at approximately 90° to a horizontal plane containing the surface of the workpiece 16. The light spot 26 illuminates a surface confronting the light source 18 of each successive workpiece 16.

The light source 18 of inspection system 17 may be a white-light light emitting diode (LED), a set of colored LED's with combined outputs to provide white light, or another suitable solid-state light emitter. As used herein, white light is considered to be a range of wavelengths in the electromagnetic spectrum that is visible to the human eye and, preferably, constitutes the entire visible spectrum. However, the invention is not so limited as the light source 18 may emit white light within a plurality of discrete sub-ranges of wavelengths within the visible white spectrum. Particularly useful light sources 18 include the NSPW500BS lamp-type LED commercially available from Nichia Corporation of Japan, which is characterized by chromaticity coordinates of (0.310, 0.320), and the LXHL-LW3C LUXEON® lamp-type LED commercially available from Lumileds Lighting, LLC (San Jose, Calif.), which is characterized by a Lambertian beam pattern and outputs 65 lumens at 700 milliamperes (mA). The optical lens 24 may be, for example, a double-concave lens having two inward curved surfaces and negative focal lengths. The intensity of the light output by light source 18 may be modulated, and the sensing of the reflected light performed at the modulation frequency of the light output to reject ambient noise. Another type of light source usable as light source 18 converts a portion of the light emitted from a blue or ultraviolet LED by making use of phosphor, so as to produce white light.

With continued reference to FIG. 1, the inspection system 17 further includes a stationary position detector 28 suspended generally above the conveyor 12. The position detector 28, which may be an optical sensor or photodetector, an inductive sensor, a capacitative sensor, or other type of known sensor, has a field of view that includes the light spot 26 on each workpiece 16 and, preferably, is located downstream from the light spot 26. The position detector 28 senses the presence or absence of a reference portion or feature (e.g., leading edge) of each workpiece 16 approaching the light spot 26. As each workpiece 16 enters its field of view, the position detector 28 generates an output signal representative of the presence of each arriving workpiece 16 and transmits that signal over a communication link or line 29 to a computer 30. The light source 18 and position detector 28 may be, for example, positioned downstream from a printing press of the process line 10, upstream from a folder and an adhesive applicator of the process line 10, or downstream from a die cutter of the process line 10.

A device, such as an encoder 32, informs the computer 30 of the line velocity of the conveyor 12 and, hence, the linear speed of each workpiece 16. The encoder 32 transmits a string of pulses over a communication link or line 33 to the computer 30 at a frequency representative of the line velocity of the conveyor 12. The encoder 32 may be a shaft encoder or any other type of conventional encoder. For example, the encoder 32 may be a rotary position transducer coupled with the shaft of a conveyor roller or with the output shaft of a motor powering the conveyor 12.

A portion of the light reflected from the polychromatic region 19 of the illuminated workpiece 16 is collected by a collection optical component 38 of the inspection system 17 and focused on a color sensor 40 of the inspection system 17. The collection optical component 38 may be, for example, a double-convex lens having two outward curved surfaces and positive focal lengths and may include a slit aperture that collimates the reflected light to restrict the collection area. The collection optical component 38 collects light reflected specularly at an angle of 45°±5° relative to the beam of light from the light source 18.

With continued reference to FIG. 1, housed inside the color sensor 40 is a plurality of, for example, three photodetectors 42, 44 and 46 each of which is adapted to detect incident light within a well-defined frequency or wavelength band of the visible region of the electromagnetic spectrum and generate an analog output signal proportional to the intensity of the detected light. For example, photodetector 42 may include an optical filter situated in the optical path that transmits light generally in the red wavelength range, photodetector 44 may include an optical filter in the optical path that transmits light generally in the green wavelength range, and photodetector 46 may include an optical filter in the optical path that transmits light generally in the blue wavelength range. The photodetectors 42, 44 and 46 will generate a set of three output signals for each of the different colors in the polychromatic region 19.

The output signal from each of the photodetectors 42, 44 and 46 will depend upon the light intensity of the reflected light in the corresponding color wavelength band for each of the different colors. The wavelength bands sensed by the photodetectors 42, 44 and 46 may collectively span the entire wavelength range of light emitted by the light source 18 or, alternatively, may sample discrete bands of wavelengths in which adjacent sensed wavelength bands are separated by intervening undetected wavelength bands.

In one embodiment of the invention, the photodetectors 42, 44 and 46 may be integrated into a single package or platform positionable relative to the arriving workpiece 16. A color sensor suitable for use as color sensor 40 is the model MCSAT color sensor package commercially available from Laser Components Instrument Group Inc. of Hudson, N.H., which includes three silicon positive-intrinsic-negative (Si-PIN) photodiodes integrated on a single chip, an appropriate dielectric spectral filter (detected wavelength bands: $\lambda_{Red}$=590 to 750 nm, $\lambda_{Green}$=490 to 610 nm, $\lambda_{Blue}$=400 to 510 nm) covering a corresponding one of the Si-PIN photodiodes, an optional infrared filter that removes wavelengths exceeding about 725 nm, and an optic window that protects the Si-PIN photodiodes from dirt and contamination while allowing reflected light to enter the sensor package. Another color sensor suitable for use as color sensor 40 is the model MCSiAT color sensor package, also commercially available from Laser Components Instrument Group Inc., which includes a hexagonal array of three (3) by nineteen (19) Si-PIN photodiodes integrated in a mosaic pattern on a single chip, an appropriate dielectric spectral filter (detected wavelength bands: $\lambda_{Red}$=590 to 750 nm, $\lambda_{Green}$=490 to 610 nm, $\lambda_{Blue}$=400 to 510 nm) covering a corresponding set of nineteen photodiodes, an optional infrared filter that removes wavelengths exceeding about 725 nm, and an optic window that protects the Si-PIN photodiodes from dirt and contamination while allowing reflected light to enter the sensor package. In the latter specific embodiment of the present invention, each set of nineteen Si-PIN photodiodes constitutes one of the photodetectors 42, 44 and 46 and the disbursed orientation of the multiple Si-PIN photodiodes over a two (2) mm detection surface provides relatively even color recognition that is substantially independent of target positioning.

The photodetectors 42, 44 and 46 are voltage biased during operation by a resistor network 41. The analog output signal (i.e., current) from each of the photodetectors 42, 44 and 46 is directed to the negative input of one of a plurality of operational amplifiers 48, 50 and 52. Resistors 54, 56 and 58 provide a negative feedback path between the output and negative input of a corresponding one of the operational amplifiers 48, 50 and 52. The resistance of each of the resistors 54, 56 and 58 determines the gain of a corresponding one of the operational amplifiers 48, 50 and 52. Each amplifier 48, 50 and 52 converts the input current from the corresponding one of photodetectors 42, 44 and 46 to an output voltage. The output voltage of the operational amplifiers 48, 50 and 52 represent the analog output of the color sensor 40 and will retain the proportionality to the detected light intensity. Operational amplifiers suitable for use as operational amplifiers 48, 50 and 52 include the MT104 Four-Channel Transimpedance Amplifier commercially available from Laser Components Instrument Group Inc. of Hudson, N.H. and the OPA267 Operational Amplifier commercially available from The Burr Brown Corporation of Tucson Ariz.

With continued reference to FIG. 1, an output signal 61, 63, 65 from each of the operational amplifiers 48, 50 and 52 (e.g., $V_{Red}$, $V_{Green}$, $V_{Blue}$), respectively, is amplified and filtered by a corresponding one of a plurality of operational amplifier circuits 60, 62 and 64 for each respective color (i.e., red, green, blue). The amplified and filtered output signals 61, 63, 65 are then converted from an analog form to a digital form by one of a plurality of analog-to-digital converters 66, 68 and 70. In certain embodiments of the invention, the analog-to-digital converters 66, 68 and 70 may be replaced by analog circuitry.

Computer 30 includes digital inputs that receive the amplified, filtered, and digitized output signals from the analog-to-digital converters 66, 68 and 70 and evaluates these output signals 61, 63, 65 as a set of ratios. For example, the computer 30 may evaluate the ratio of the red light intensity to blue light intensity, the ratio of the green light intensity to red light intensity, and the ratio of the blue light intensity to green light intensity. The color intensity ratios are independent of the intensity of reflected light focused by the collection optical component 38 on color sensor 40. This represents an advantage of the present invention over conventional color detection systems that evaluate absolute color intensities.

The color intensity ratios may be compared with a reference, such as a target standard ratio, with historical color intensity ratio information from past color intensity ratio measurements, or the color intensity ratio for the polychromatic region 19 on a previous workpiece 16. Target standard ratios may be furnished from an exemplary workpiece 16, which teaches a set of color intensity ratios to the computer 30 for comparison with color intensity ratios acquired from subsequent workpieces 16. If the color of the polychromatic region 19 illuminated by the light spot 26 changes, the color intensity ratios will also change.

Computer 30 may determine whether or not the hue(s) or color shade(s) in the polychromatic region 19 on consecutive workpieces 16 is varying among the individual workpieces 16 by detecting variations in the color intensity ratios. However, computer 30 is not determining an absolute hue or shade of color. In alternative embodiments of the present invention, the computer 30 may determine whether the color intensity ratios for the different colors characterizing the polychromatic region 19 are varying among consecutive workpieces 16 for quality control. This effectively improves the speed of the measurement in comparison with conventional systems that provide an indication of an absolute shade of color or hue. However, the computer 30 is not reading and translating any information that may or may not be encoded in the polychromatic region 19. This effectively improves the speed of the measurement in comparison with conventional systems that decode information encoded in the polychromatic region 19.

In yet other alternative embodiments, the computer 30 may also use the color intensity ratios to determine whether or not the polychromatic region 19 is accurately positioned in two-dimensions relative to the edges of the workpiece 16. This may be particularly useful in die cutting operations for quality control. If variations are detected, the computer 30 may provide an alert to a parent machine of process line 10, may be used as feedback information to adjust the process, or may be used to reject defective workpieces 16. This takes advantage of the ability to sense contrast in the color intensity ratios between polychromatic region 19 and regions of a different on workpiece 16 near polychromatic region 19, as the light spot 26 moves across the surface of the workpiece 16.

The computer 30 synchronizes the color intensity ratios with output signals 61, 63, 65 from the position detector 28 and encoder 32. The trigger signal from the position detector 28 informs the computer 30 that one of the workpieces 16 is arriving for reading and thereby triggers recording of the reflected light intensities. Output signals 61, 63, 65 from the encoder 32 permit the computer 30 to relate the determined color intensity ratios with an absolute location on the workpiece 16. The sampling length may be equal to one or more pulses received from the encoder 32. For each workpiece 16, the color intensity ratios measured as a function of location on the workpiece 16 may be stored by the computer 30 for future use. For example, this may be useful for mapping the color intensity ratios as a function of position on workpiece 16 along the path traced by the light spot 26 from the light source 18. Position detector 28 also supplies a trigger signal to computer 30 when another feature (e.g., a trailing edge) of workpiece 16 is detected and the computer 30 responds to the trigger signal by discontinuing the detection or recording of the reflected light intensities.

By comparing the color intensity ratios between consecutive workpieces 16, the computer 30 differentiates between a variety of color differences. Despite changing conditions, such as workpiece vibration, that may vary in the reflected light intensity, the ratios of the color intensities remain constant and are independent of the actual received light intensities. Analyzing color intensity ratios also rejects changes in the ambient lighting conditions in the environment of the process line 10, as the ambient lighting is also reflected from the workpiece 16 and polychromatic region 19 and also directly enters the color sensor 40. The computer 30 can accurately measure the color of successive workpieces 16 at relatively high speed and, thereby, efficiently verify every workpiece 16.

Figure 2A:
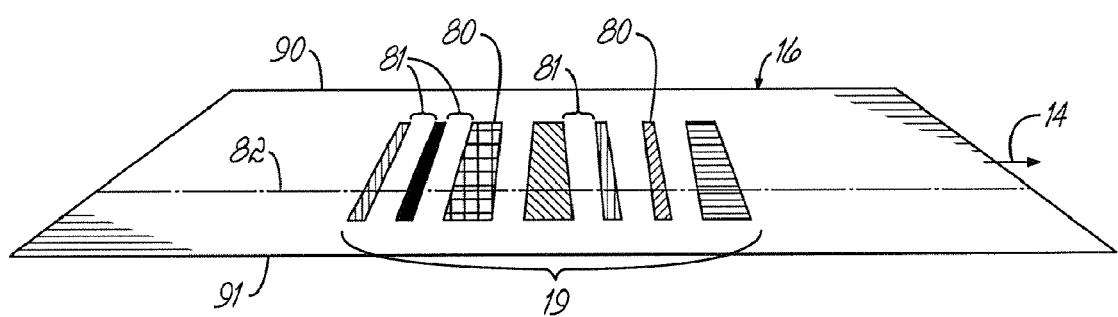
FIGS. 2A and 2B are diagrammatic views of workpieces each including a polychromatic region.

With reference to FIG. 2A, the polychromatic region 19 on workpiece 16 may generally include a plurality of colored bars 80 disposed side-by-side in which intervening spaces 81 of a contrasting color separate adjacent bars 80. The bar/space pattern defines one or more alphanumeric values in accordance with a predefined standard. Each of the bars 80 has an associated color that is assigned when the polychromatic region 19 is printed or otherwise formed on workpiece 16. Each bar 80 may have the same color or a different color and, typically, each bar 80 has the same color. The light spot 26 (FIG. 1) moves along a longitudinal axis 82 substantially parallel to edges 90, 91 as the workpiece 16 moves in travel direction 14. The coloration (i.e., the color intensities) measured by the color sensor 40 varies because of the colors of the bars 80 and the presence of the spaces 81.

The inspection system 17 determines the uniformity and repeatability of the bars 80 among polychromatic region 19 on successive workpieces 16. Variations may occur during the printing process that the inspection system 17 is capable of detecting and taking corrective measures. The inspection system 17 is capable of sensing substantially the entire visible spectrum of colors potentially available for printing or forming bars 80 or at least the portion(s) of the visible spectrum characterizing the colors in the bars 80. However, the inspection system 17 does not read or translate any information encoded in the bars 80 of the polychromatic region 19, which effectively improves the speed of the measurement in comparison with conventional systems that decode this information. This applied to polychromatic regions 19 with information encoded in a string of polychromatic symbols that differ from bars 80.

Figure 2B:
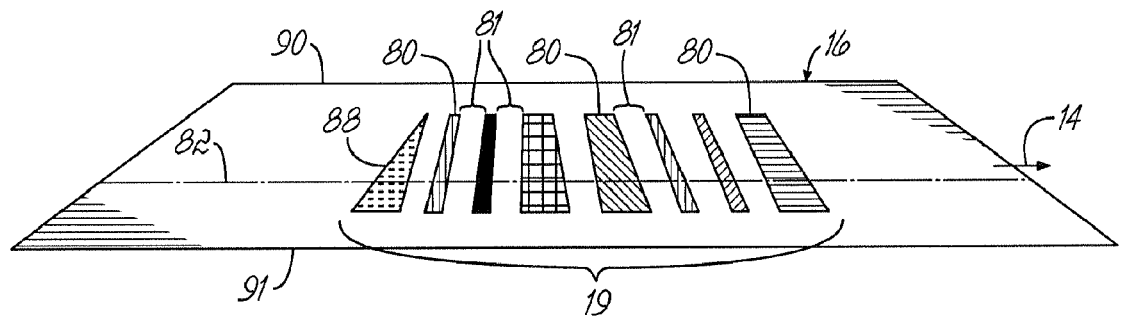

With reference to FIG. 2B in which like reference numerals refer to like features in FIG. 2A, polychromatic region 19 may include one or more bars 88 having a geometric shape, a triangle in this case. The inspection system 17 can sense a change in the position of the polychromatic region 19 in a direction orthogonal to the direction of motion 14 (i.e., lateral position relative to a feature, such as edges 90 and 91, on workpiece 16) by evaluating the color intensity ratios of the geometrically shaped bar 88. The change in the lateral position is sensed by determining the travel distance or displacement of the workpiece 16 in the travel direction 14 across which the color intensity ratio characteristic of bar 88 is sensed by the color sensor 40. A variation in this displacement, as compared with a standard displacement from either a reference standard, a historical displacement, or the displacement of the previous workpiece 16, indicates that the lateral position of the bar 88 on the particular workpiece 16 is anomalous. If the anomaly continues and is not an isolated event for one or even a few workpieces 16, corrective measures may be required in the process of applying the polychromatic region 19 on successive workpieces 16.

The color discrimination devices and methods of the various embodiments of the present invention provide high-speed evaluations of colorimetric values, as compared with the capabilities of conventional color detection systems, with relatively inexpensive equipment requiring minimal maintenance. The color discrimination devices are capable of verifying the spectral uniformity of each of the successive workpieces moving through a production line. The increased speed of the measurements arises from the parallel acquisition and processing of the colorimetric values, with 25 microseconds being typical. The devices and methods of the invention offer ease of operation and permit the measurement of small targets (e.g., 1 mm).

A solid-state light source is used in the present invention, in contrast to the conventional halogen light source traditionally used in conventional color detection systems. The solid-state light source reduces heat and drift and is long lived, even when mounted on vibrating machinery. Because of the ratiometric conversion of the light intensities determined from the output of the color sensor, field calibration is not required as system components age. The present invention also permits accurate determinations of the color ratios in polychromatic regions, such as solid regions, color indicia, or color patterns, on workpieces characterized by specular surfaces that cause variations in the reflected light intensity.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

What is claimed is:

1. A device for inspecting a moving workpiece having a polychromatic region, comprising:

a solid-state light source adapted to emit light in a range of wavelengths, said light source positioned relative to the moving workpiece to illuminate the polychromatic region with the light;

a first photodetector positioned relative to the moving workpiece to intercept a first portion of the light reflected by the polychromatic region, said first photodetector adapted to detect an intensity of the first portion of the light within a first wavelength band defined within the range of wavelengths and to generate a first output signal proportional to the intensity of the first portion of the light within the first wavelength band;

a second photodetector positioned relative to the moving workpiece to intercept a second portion of the light reflected by the polychromatic region, said second photodetector adapted to detect an intensity of the second portion of the light within a second wavelength band defined within the range of wavelengths and to generate a second output signal proportional to the intensity of the second portion of the light within the second wavelength band; and a computer electrically coupled with said first and second photodetectors, said computer configured to determine a ratio of the first and second output signals and to compare said ratio with a reference so as to ascertain a variation in said ratio relative to the reference.

2. The device of claim 1 wherein said light source is a light emitting diode.

3. The device of claim 1 wherein the range of wavelengths is within a visible portion of the electromagnetic spectrum, and each of the first and second wavelength bands is within the visible portion of the electromagnetic spectrum, and said first and second photodetectors are configured to respectively detect the first and second portions of the light in the first and second wavelength bands within the visible portion of the electromagnetic spectrum.

4. The device of claim 1 further comprising:
a single electronics package integrating said first and second photodetectors.

5. A method for inspecting a polychromatic region on a moving workpiece, comprising:
illuminating the moving workpiece with light that includes a range of wavelengths;
detecting a first intensity of the light reflected from the polychromatic region within a first wavelength band in the range of wavelengths;
detecting a second intensity of the light reflected from the polychromatic region within a second wavelength band in the range of wavelengths;
determining a ratio of the first intensity to the second intensity; and
comparing the determined ratio with a reference to ascertain a variation in the determined ratio relative to the reference.

6. The method of claim 5 wherein the range of wavelengths is within a visible portion of the electromagnetic spectrum.

7. The method of claim 5 wherein the reference is established by averaging the ratio of the first intensity to the second intensity previously evaluated for the polychromatic region on a plurality of workpieces.

8. The method of claim 5 wherein the polychromatic region is a color barcode including a plurality of bars each having a color, and determining the ratio further comprises:
determining the ratio of the first intensity to the second intensity for at least one of the plurality of bars.

9. The method of claim 5 wherein the workpiece has an edge and is moving in a travel direction, and the polychromatic region is a color barcode including at least one bar having a dimension that varies in a direction across the workpiece orthogonal to the travel direction and relative to the edge of the workpiece, and determining the ratio further comprises:
determining a change in a location of the at least one bar on the moving workpiece relative to the edge.

10. The method of claim 9 wherein determining the change in the location further comprises:
measuring a displacement of the moving workpiece in the travel direction across which the ratio is detected; and
comparing the displacement of the moving workpiece with another reference to ascertain the change in the location of the at least one bar relative to the edge.

11. The method of claim 5 further comprising:
sensing a first feature of the moving workpiece; and
detecting the first and second intensities of the reflected light after the first feature is sensed.

12. The method of claim 11 further comprising:
sensing a second feature of the moving workpiece; and
discontinuing detection of the first and second intensities of reflected light after the second feature is sensed.

13. A method for inspecting a plurality of polychromatic regions each carried on a corresponding one of a plurality of moving workpieces, comprising:
illuminating each of the plurality of moving workpieces with light that includes a range of wavelengths;
determining a ratio of a light intensity reflected from each of the polychromatic regions within a first wavelength band in the range of wavelengths to a light intensity reflected from each of the polychromatic regions within a second wavelength band in the range of wavelengths; and
comparing the determined ratio for first and second workpieces among the plurality of moving workpieces to detect a variation in a color within the polychromatic region between the first and second workpieces.

14. The method of claim 13 wherein the polychromatic region has a pattern containing encoded information, and determining the ratio further comprises:
determining the ratio without decoding any information in the pattern.

15. The method of claim 13 wherein comparing the determined ratio for the first and second workpieces further comprises:
determining a position of the polychromatic region relative to a feature on each of the first and second workpieces.

16. The method of claim 15 wherein determining the position further comprises:
sensing a feature on each of the workpieces; and
determining a location of the polychromatic region relative to the sensed feature on each of the first and second workpieces.

17. The method of claim 16 wherein determining the location further comprises:
measuring a linear speed at which each of the plurality of workpieces is moving when illuminated with the light.

18. The method of claim 13 wherein illuminating each of the plurality of moving workpieces with the light further comprises:
illuminating each of the plurality of moving workpieces with a light spot that emits the light within the range of wavelengths;
illuminating each of the plurality of moving workpieces with ambient light of a varying intensity and within the range of wavelengths; and
rejecting variations in the varying intensity of the ambient light when the ratio is determined for first and second workpieces.

19. The method of claim 13 further comprising:
detecting the light intensity reflected from the polychromatic region within the first wavelength band in the range of wavelengths with a first detector sensitive to light within the first wavelength band; and
detecting the light intensity reflected from the polychromatic region within the second wavelength band in the range of wavelengths with a second detector sensitive to light within the second wavelength band.

* * * * *

UNITED STATES PATENT AND TRADEMARK OFFICE
CERTIFICATE OF CORRECTION

PATENT NO.       : 7,365,854 B2                                              Page 1 of 1
APPLICATION NO.  : 10/908221
DATED            : April 29, 2008
INVENTOR(S)      : Martin Gaon It is certified that error appears in the above-identified patent and that said Letters Patent is hereby corrected as shown below:

In Claim 16, Column 10, line 35, after "the", insert --first and second--.

Signed and Sealed this

Tenth Day of March, 2009

JOHN DOLL
*Acting Director of the United States Patent and Trademark Office*